United States Patent [19]
Kilbane, II

[11] Patent Number: 5,358,869
[45] Date of Patent: Oct. 25, 1994

[54] MICROBIAL CLEAVAGE OF ORGANIC C-S BONDS

[75] Inventor: John J. Kilbane, II, Woodstock, Ill.

[73] Assignee: Institute of Gas Technology, Chicago, Ill.

[21] Appl. No.: 850,081

[22] Filed: Mar. 12, 1992

Related U.S. Application Data

[63] Continuation-in-part of Ser. No. 461,389, Jan. 5, 1990, Pat. No. 5,104,801, and a continuation-in-part of Ser. No. 640,931, Jan. 14, 1991, Pat. No. 5,198,341, which is a continuation of Ser. No. 461,265, Jan. 5, 1990, Pat. No. 5,002,888.

[51] Int. Cl.$^5$ .............. C12S 1/00; C10G 32/00; C10L 5/00
[52] U.S. Cl. .................. 435/282; 435/281; 435/262; 44/622
[58] Field of Search .............. 435/262, 281, 282, 821, 435/822, 71.1, 71.2, 71.3; 44/622

[56] References Cited

U.S. PATENT DOCUMENTS

| | | | |
|---|---|---|---|
| 2,641,564 | 6/1953 | Zobell | 435/282 |
| 4,206,288 | 6/1980 | Detz et al. | 435/267 |
| 4,562,156 | 12/1985 | Isbester et al. | 435/282 |
| 4,632,906 | 12/1986 | Kopacz | 435/282 |
| 4,659,670 | 4/1987 | Stevens, Jr. et al. | 435/262 |
| 4,808,535 | 2/1989 | Isbister | 435/252.1 |
| 4,851,350 | 7/1989 | Stevens, Jr. et al. | 435/262 |
| 5,002,888 | 3/1991 | Kilbane | 435/252.31 |
| 5,092,909 | 3/1992 | Werner et al. | 435/262 |
| 5,094,668 | 3/1992 | Kern et al. | 435/282 |
| 5,104,801 | 4/1992 | Kilbane | 435/282 |
| 5,132,219 | 7/1992 | Kilbane | 435/195 |
| 5,198,341 | 3/1993 | Kilbane | 435/42 |
| 5,232,854 | 8/1993 | Monticello | 435/282 |

FOREIGN PATENT DOCUMENTS 9209706  6/1992  World Int. Prop. O. .......... 435/262

OTHER PUBLICATIONS

Sorkhoh, N. A. et al., "Crude Oil and Hydrocarbon-Degrading Strains of *Rhodococcus rhodochrous* Isolated from Soil and Marine Environments in Kuwait," *Environmental Pollution*, 65, 1990, pp. 1–17.

Eligwe, C. A., "Microbial Desulfurization of Coal," *Fuel*, 67:451–458 (1988).

Hartdegen, F. J., Coburn, J. M., and Roberts, R. L., "Microbial Desulfurization of Petroleum," *Chem. Eng. Progress*, vol. 80, No. 5 pp. 63–67 (1984).

Eckart, V., Hieke, W., Bauch, J., and Gentzsch, H., "Microbial Desulfurization of Petroleum and Heavy Petroleum Fractions. 1. Studies On Microbial Aerobic Desulfurization of Romashkino Crude Oil," Zentralbl. Microbiol. 135(8), 674–681 (1980), Chemical Abstracts, vol. 94, No. 142230q, (1981).

Eckhart, V., Hieke, W., Bauch, J., and Gentzsch, H., "Microbial Desulfurization of Petroleum and Heavy Petroleum Fractions. 3. Change in the Chemical Composition of Fuel-D-Oil by Microbial Aerobic Desulfurization," Zentralbl. Microbial. 137(4), 270–279 (1982), Chemical Abstracts, vol. 97, No. 147259c, (1982).

Lee, Min Jai and Oh, Myung Soo, "Isolation, Identification, and Physiological Characteristics of Some Sulfur-Reducing Microbes," misaengmul Hakhoe Chi, 10(4), 175–190, (1972) Chemical Abstracts, vol. 78, No. 94605m (1973).

Bauch, J., Gentzsch, H., Hieke, W., Echart, V., Koehler, M., and Babenzin, H. D., "Oxidative Microbiological Dusulfurization of Heavy Petroleum Fractions,"

(List continued on next page.)

*Primary Examiner*—Michael G. Wityshyn
*Assistant Examiner*—T. J. Reardon
*Attorney, Agent, or Firm*—Speckman, Pauley & Fejer

[57] ABSTRACT

A microbial process for selective cleavage of organic C—S bonds which may be used for reducing the sulfur content of sulfur-containing organic carbonaceous materials, Microorganisms of *Rhodococcus rhodochrous* and *Bacillus sphaericus* have been found which have the ability of selective cleavage of organic C—S bonds. Particularly preferred microorganisms are *Rhodococcus rhodochrous* strain ATCC 53968 and *Bacillus sphaericus* strain ATCC 53969 and their derivatives.

9 Claims, No Drawings

OTHER PUBLICATIONS

DD Patent 108,533, 20 Sep. (1974), Chemical Abstracts, vol. 83, No. 82530y (1975).

Yuda, Sadayuki, "Petroleum Desulfurization by *Pseudomonas haconensis*," Japanese Patent 75.107,002, 23 Aug. (1975) Chemical Abstracts, vol. 84, No. 46982j (1976).

Lee, M. J., Hah, Y. C., and Lee, K. W., "Dusulfurization of Petroleum by Microorganisms. I. Isolation and Identification of Sulfur-Oxidizing and Reducing Bacteria," Haksurwon Nonmunjip, Cha'yon Kwahak P'yon 12, 21–49, (1973), Chemical Abstracts, vol. 85, No. 156414d (1976).

Lee, M. J., Hah, Y. C. and Lee, K. W., "Desulfurization of Petroleum by Microorganisms. III. Desulfurization of Petroleum by Contact Reaction with Desulfurizing Bacteria," Haksurwon Nonmunjip, Cha'yon Kwahak P'yon 12, 73–95, (1973), Chemical Abstracts, vol. 85, No. 145448s (1976).

Malik, K. A., "Microbial Removal of Organic Sulfur from Crude Oil and the Environment. Some New Perspectives," Process Biochem., 13(9), 10–13, (1978).

Knecht, A. T., Jr., Thesis Dissertation, Louisiana State University, Order No. 621235 (1961).

Laborde, A. L., and Gibson, D. T., "Metabolism of Dibenzothiophene by a *Beijerinckia* Species," Appl. Environ Microbial., 34, 783–790 (1977).

Hou, C. T. and Laskin, A. I., "Microbial Conversion of Dibenzothiophene," Dev. Ind. Microbial., 17, 351–362 (1976).

Isbister, J. D. and Kobylinski, E. A., "Microbial Desulfurization of Coal in Processing and Utilization of High Sulfur Coals," Coal Science and Technology Series, No. 9, 627, Attia Y. A., Ed. Amsterdam: Elsevier (1985).

Kodama, K., Nakatini, S., Umehara, K., Shimizu, K., Minoda, Y., and Yamada, K., "Microbial Conversion of Petrosulfur Compounds: Isolation and Identification of Products from Dibenzothiophene," Agr. Biolog. Chem., 34, 1320–1324 (1970).

Monticello, D. J., Bakker, D., and Finnerty, W. R., "Plasmid Mediated Degradation of Dibenzothiophene by *Pseudomonas* Species," Appl. environ. Microbial., 49, 756–760 (1985).

Kargi, F. and Robinson, J. M., "Microbial Oxidation of Dibenzothiophene by the Thermophilic Organisms *Sulfolobus acidocaldarius*," Biotech. and Bioeng., 126, 687–690 (1984).

Kilbane, John J., "Sulfur-Specific Microbial Metabolism of Organic Compounds," Bioprocessing of Coals Workshop, Tysons Corner, Va., Aug. 16–18, 1988.

Omori, T., Monna, L., Saiki, Y., and Kodama, T., "Desulfurization of Dibenzothiophene by *Corynebacterium sp.* Strain SY1" App. & Environ. Microbiol. 58, 3, 911–915, Mar. (1992).

MICROBIAL CLEAVAGE OF ORGANIC C-S BONDS

The U.S. Government has rights in this invention as set forth in Department of Energy Contract No. DE-AC22-85PC81201.

CROSS REFERENCE TO RELATED APPLICATIONS

This application is a continuation-in-part of copending applications Ser. No. 07/461,389, filed Jan. 5, 1990 now U.S. Pat. No. 5,104,801 and Ser. No. 07/640,931, filed Jan. 14, 1991, now U.S. Pat. No. 5,198,341 the latter of which is a continuation of Ser. No. 07/461,265, filed Jan. 5, 1990 now U.S. Pat. No. 5,002,888.

BACKGROUND OF THE INVENTION

1. Field of the Invention

This invention relates to a process for microbial cleavage selectively of organic C—S bonds and removal of sulfur from sulfur-containing organic carbonaceous material thereby. Useful for use in the process of this invention are microorganisms which have the ability of selective cleavage of organic C—S bonds, such as microorganisms *Rhodococcus rhodochrous* and *Bacillus sphaericus* and their derivatives. Particularly preferred are *Rhodococcus rhodochrous* strain ATCC No. 53968 and *Bacillus sphaericus* strain ATCC No. 53969 and their derivative microorganisms. The process of this invention is particularly useful in removal of organic sulfur from fossil fuels, such as sulfur-containing coal and oils.

2. Description of the Prior Art

Sulfur content of carbonaceous fuels, such as coals and oils, has prevented utilization of a considerable amount of such materials due to deleterious effect upon the environment. Inorganic pyritic sulfur and organically bound sulfur may each constitute as much as about 3.5 weight percent of the coal. Pyritic sulfur has been found to be relatively easy to remove by techniques including heavy media separation, selective agglomeration, flotation, jigging, magnetic separation, leaching and hydrosulfurization. Microbial metabolism of inorganic pyritic sulfur by its oxidation using bacteria such as Thiobacillus and Sulfolobus species is known. Eligwe, C. A., "Microbial Desulfurization of Coal," *Fuel,* 67: 451–458 (1988). These chemolithotropic organisms can utilize inorganic pyritic sulfur compounds as energy sources and are capable of removing 90% or more of the inorganic pyritic sulfur from coal within a few days. *Thiobacillus ferrooxidans* is taught by U.S. Pat. No. 4,206,288 as suitable for removal of pyritic sulfur from coal.

*Bacillus sulfasportare* ATCC 39909 has been taught by U.S. Pat. No. 4,632,906 to be capable of sulfur removal from coal, without differentiation between pyritic and organic sulfur. An unidentified mixed culture of seven gram negative rods (ATCC 39327) prepared by growth in situ enriched with sulfur compounds and subsequently grown in the presence of coal has been shown to reduce the sulfur content of coal by about 20 percent per day with a substantial portion being reduction of organic sulfur as taught by U.S. Pat. No. 4,659,670.

Removal of sulfur from petroleum hydrocarbons by contact with hydrogen in the presence of hydrogenase-producing microorganisms *Desulfovibrio desulfuricans* and Sporovibrio followed by removal of sulfur in the form of gaseous products is taught by U.S. Pat. No. 2,641,564. Removal of sulfur from petroleum by Pseudomonas is taught by Hartdegen, F. J., Coburn, J. M., and Roberts, R. L., "Microbial Desulfurization of Petroleum," Chem. Eng. Progress, Vol. 80, No. 5, pp. 63–67 (1984) to be by C—C cleavage. General teachings of various Pseudomonas for removal of sulfur from petroleum are in Eckart, V., Hieke, W., Bauch., J., and Gentzsch, H., "Microbial Desulfurization of Petroleum and Heavy Petroleum Fractions. 1. Studies on Microbial Aerobic Desulfurization of Romashkino Crude Oil," Zentralbl. Microbiol. 135(8), 674–681 (1980), Chemical Abstracts, Vol. 94, No. 142230q, (1981); Eckart, V., Hieke, W., Bauch, J., and Gentzsch, H., "Microbial Desulfurization of Petroleum and Heavy Petroleum Fractions. 3. Change in the Chemical Composition of Fuel-D-Oil by Microbial Aerobic Desulfurization," Zentralbl. Microbiol. 137(4), 270–279 (1982), Chemical Abstracts, Vol. 97, No. 147259c, (1982); Lee, Min Jai and Oh, Myung Soo, "Isolation, Identification, and Physiological Characteristics of Some Sulfur-Reducing Microbes," Misaengmul Hakhoe Chi, 10(4), 175–190, (1972) Chemical Abstracts, Vol. 78, No. 94605m (1973); Bauch, J., Gentzsch, H., Hieke, W., Eckart, V., Koehler, M., and Babenzin, H. D., "Oxidative Microbiological Desulfurization of Heavy Petroleum Fractions," DD Patent 108,533, Sep. 20 (1974), Chemical Abstracts, Vol. 83, No. 82530y (1975); and Yuda, Sadayuki, "Petroleum Desulfurization by *Pseudomonas haconensis,*" Japanese Patent 75.107,002, Aug. 23 (1975). Chemical Abstracts, Vol. 84, No. 46982j (1976). *Thiobacillus thiooxidans* has been identified as the most effective S-oxidizer and *Pseudomonas putrefaciens* and *Desulfovibrio desulfuricans* the most effective S-reducers in microbial removal of sulfur from petroleum, Lee, M. J., Hah, Y. C., and Lee, K. W., "Desulfurization of Petroleum by Microorganisms. I. Isolation and Identification of Sulfur-Oxidizing and -Reducing Bacteria," Haksurwon Nonmunjip, Cha'yon Kwahak P'yon 12, 21–49, (1973), Chemical Abstracts, Vol. 85, No. 156414d (1976); Lee, M. J., Hah, Y. C., and Lee, K. W., "Desulfurization of Petroleum by Microorganisms. III. Desulfurization of Petroleum by Contact Reaction with Desulfurizing Bacteria," Haksurwon Nonmunjip, Cha'yon Kwahak P'yon 12, 73–95, (1973), Chemical Abstracts, Vol. 85, No. 145448s (1976).

Organic sulfur which is chemically bound within the carbonaceous molecule must be removed either by chemical or biological means. Dibenzothiophene (DBT) is the organosulfur compound most persons consider representative of the form in which organic sulfur exists in naturally occurring organic carponaceous fuels such as coal and oil and is the compound upon which the microbial metabolism of organosulfur compounds has focused. Study of DBT metabolism has been pursued by several researchers who have isolated organisms capable of metabolizing DBT including Acinetobacter, Malik, K. A., "Microbial Removal of Organic Sulfur from Crude Oil and the Environment: Some New Perspectives," Process Biochem., 13(9), 10–13 (1978); Arthrobacter, Knecht, A. T., Jr., Thesis Dissertation, Louisiana State University, Order No. 621235 (1961); Beijerinckia, Laborde, A. L., and Gibson, D. T., "Metabolism of Dibenzothiophene by a Beijerinckia Species," Appl. Environ. Microbiol., 34, 783–790 (1977); Rhizobium, Malik, K. A., (supra); Pseudomonas, Hou, C. T. and Laskin, A. I., "Microbial Conversion of Dibenzothiophene," Dev. Ind. Microbiol., 17, 351–362 (1976); Isbister, J. D. and Kobylinski, E. A., "Microbial Desulfurization of Coal in Processing and Utilization of High Sulfur Coals," Coal Science and Technology Series, No. 9, 627, Attia, Y. A., Ed. Amsterdam: Elsevier (1985); Knecht, A. T., Jr., (supra); Kodama, K., Nakatani, S., Umehara, K., Shimizu, K., Minoda, Y., and Yamada, K., "Microbial Conversion of Petrosulfur Compounds: Isolation and Identification of Products from Dibenzothiophene," Agr. Biolog. Chem., 34, 1320–1324 (1970); Monticello, D. J., Bakker, D., and Finnerty, W. R., "Plasmid Mediated Degradation of Dibenzothiophene by Pseudomonas Species," Appl. Environ. Microbiol., 49, 756–760 (1985); Sulfolobus, Kargi, F. and Robinson, J. M., "Microbial Oxidation of Dibenzothiophene by the Thermophilic Organisms *Sulfolobus acidocaldarius,*" Biotech. and Bioeng., 126, 687–690 (1984). The pathway of microbial degradation of DBT in each of the above cases except in Isbister, et al., (supra), is by C—C bond cleavage according to microbial degradation pathways of DBT originally established by Kodama, et al., (supra). Microbial degradation of organic sulfur-containing carbonaceous materials by C—C bond cleavage results in the loss of a large portion of the calorific value of the carbonaceous fuel. According to the Kodama, et al. (supra), C—C bond cleavage microbial degradation of DBT, sulfur-containing end products are 3-hydroxybenzothiophene sulfoxide, 2-formyl benzothiophene, or benzothiophene. It is, therefore, desirable to follow a microbial degradation route which removes sulfur from the molecule without removing carbon from the molecule, thereby retaining calorific value of the fuel to a greater degree than is possible by carbon degradative pathways. Such sulfur-specific metabolism of the organic substrates requires cleavage of carbon—sulfur bonds in the organic sulfur-containing molecule. In the case of sulfur specific metabolism of dibenzothiophene, the organic end product is 2-hydroxybiphenyl. This C—S cleavage pathway may proceed according to dibenzothiophene→dibenzothiophene sulfoxide→dibenzothiophene sulfone→dibenzothiophene sulfonate→2-hydroxybiphenyl+inorganic sulfate. The monohydroxy product of this C—S cleavage route distinguishes it from routes leading to significant amounts of bihydroxybiphenyl.

The only prior microorganism known to the present inventor allegedly capable of degradation of DBT by C—S cleavage is a Pseudomonas species as described by Isbister, (supra), and Pseudomonas ATCC 39381, as set forth in U.S. Pat. No. 4,562,156. The ATCC 39381 culture on deposit does not possess the C—S cleavage trait and the depositors of the culture have stated that the culture on deposit cannot be replaced as such cultures having the C—S cleavage trait to their knowledge do not exist. (4th Department of Energy Preparation, Utilization and Environmental Control Contractors Conference, U.S. Dept. of Energy, Pittsburgh Energy Technology Center, Pittsburgh, Pa. 15236, U.S.A., 1988). Mixed cultures obtained through growth under sulfur limited conditions have been capable of selective removal of sulfur from DBT, Kilbane, John J., "Sulfur-Specific Microbial Metabolism of Organic Compounds," Bioprocessing of Coals Workshop, Tysons Corner, Va., Aug. 16–18, 1988.

SUMMARY OF THE INVENTION

It is an object of this invention to provide a microbial process for selective removal of organically bound sulfur from sulfur-containing organic carbonaceous materials.

It is another object of this invention to provide a microbial process for selective sulfur removal from organic sulfur-containing fossil and fossil derived fuels.

It is yet another object of this invention to provide a microorganism and process capable of specific cleavage of C—S bonds in reactions of organic carbonaceous materials, such as in organic synthesis and in recycling operations, such as recycling of rubber products.

It is still another object of this invention to provide a process using a microorganism which is stable and retains its organic sulfur specific characteristics under process conditions using the microorganism for cleavage of organic C—S bonding.

It is another object of this invention to provide a microorganism and process for specific sulfur removal from dibenzothiophene resulting in the primary organic product of 2-hydroxybiphenyl.

The above and other objects and advantages, as will become evident upon reading this description, can be achieved by contacting a sulfur-containing organic carbonaceous material with a microorganism which has the ability of selective cleavage of organic C—S bonds and production of inorganic sulfate when grown in a growth medium comprising mineral nutrients and an assimilable source of carbon in the presence of oxygen and the substantial absence of a sulfur-containing compound except the sulfur-containing organic carbonaceous material. *Rhodococcus rhodochrous* and *Bacillus sphaericus* microorganisms and their derivatives having the above properties are particularly preferred.

The above and other objects and advantages, as will become evident from reading of this description, have been achieved by the biologically pure culture of a mutant microorganism which has been produced, identified, and subjected to processes as set forth in further detail and identified as *Rhodococcus rhodochrous*. The culture has been deposited under the Budapest Treaty with American Type Culture Collection, 12301 Park Lawn Drive, Rockville, Md., U.S.A. 20852, Nov. 28, 1989 and assigned ATCC Number 53968.

*Rhodococcus rhodochrous* ATCC No. 53968 may be prepared by inoculating with mixed bacteria derived from sites having present materials of C—S bonding desired to be cleaved a growth medium comprising mineral nutrients, an assimilable source of carbon, and in substantial absence of a sulfur-containing compound, except compounds having sulfur present only in C—S bonding of the type desired to be cleaved; growing the bacterial culture in the presence of oxygen at temperatures about 20° to about 34° C. and in the substantial absence of a sulfur-containing compound except compounds having sulfur present only in C—S bonding of the type desired to be cleaved for sufficient time to selectively produce *Rhodococcus rhodochrous* ATCC No. 53968 which has the property of sulfur metabolism by selective cleavage of C—S bonds in organic carbonaceous materials.

Sulfur content of sulfur-containing organic carbonaceous material may be reduced by contacting such sulfur containing organic carbonaceous material with the microorganism *Rhodococcus rhodochrous* strain ATCC No. 53968. The process is especially suitable for use where the sulfur-containing carbonaceous material is coal or hydrocarbon oil. Continuous growth of *Rhodococcus rhodochrous* ATCC No. 53968 in the presence of sulfur-containing coal results in the removal of more than 80 percent, and preferably more than 90 percent, of the organically bound sulfur. The process for reducing the sulfur content of the sulfur-containing organic carbonaceous material occurs by cleavage of organic C—S bonds by the microorganism *Rhodococcus rhodochrous* strain ATCC No. 53968. The organic sulfur selective mutant microorganism *Rhodococcus rhodochrous* ATCC 53968 has the ability to selectively reduce the sulfur content of sulfur-containing organic carbonaceous material by cleavage of organic C—S bonds by production of inorganic sulfate when grown in a growth medium comprising mineral nutrients and an assimilable source of carbon in the substantial absence of a sulfur-containing compound except the sulfur-containing organic carbonaceous material, and in the presence of oxygen at temperatures about 20° to about 34° C. Derivative microorganisms of *Rhodococcus rhodochrous* ATCC 53968 also have the ability to selectively reduce the sulfur content of sulfur-containing organic carbonaceous material by cleavage of organic C—S bonds in the same fashion.

The above and other objects and advantages have also been achieved by the microorganism which has been produced, identified, and subjected to the processes set forth in further detail and identified as *Bacillus sphaericus*. The culture has been deposited under the Budapest Treaty with American Type Culture Collection, 12301 Park Lawn Drive, Rockville, Md., U.S.A., 20852, Nov. 28, 1989 and assigned ATCC Number 53968. These microorganisms, their production and use for selective cleavage of organic C—S bonds, their derivatives and their use for selective cleavage of organic C—S bonds are more fully described in copending, commonly owned U.S. patent application Ser. No. 07/640,931, filed Jan. 14, 1991, now U.S. Pat. No. 5,198,341 containing the disclosure of U.S. Pat. No. 5,002,888, and which is incorporated herein by reference in its entirety.

DESCRIPTION OF PREFERRED EMBODIMENTS

Environmental cultures having a known history of exposure to organosulfur compounds as well as enrichment cultures using as carbon sources acetate, benzene, benzoic acid, ethanol, glucose, glycerol, nutrient broth, succinate, and toluene and organic sulfur compounds benzothiophene, dibenzothiophene, thiophene, trithiane, produced bacterial cultures capable of metabolizing each of the organic sulfur compounds used. All of the environmental isolates and enrichment cultures tested were found to metabolize organosulfur compounds by initiating biodegradation at the carbon—carbon bond except for a mixed culture enriched with thiophene as its sole source of sulfur which was shown to be capable of carbon—sulfur bond cleavage for about 20% of its products, the remaining 80% being the result of carbon—carbon bond cleavage. The most successful microorganism for sulfur utilization from organosulfur compounds was Pseudomonas isolated from enrichment cultures employing DBT as the sole source of sulfur. This Pseudomonas species while capable of utilizing organically bound sulfur failed to show selectivity and specificity for the oxidation of carbon—sulfur bonds. This shows the failure of enrichment culture development of a naturally occurring microorganism showing specificity for oxidation of organic C—S bonds. Thus, an unnatural, selective mutation process must be utilized to develop a microorganism having such selective sulfur metabolism.

Microorganisms having sulfur-specific metabolic abilities with respect to organic substrates were developed by selection through a continuous culture coal bioreactor/selectostat in which nutrients and organically bound sulfur not normally found in living tissue may be supplied in the substantial absence of other available sulfur such as sulfates, vitamins, amino acids and the like. The growth media should supply organic and inorganic nutrients for good microorganism growth, but be devoid of inorganic and organic sulfur-containing compounds except those organic sulfur-containing compounds desired to be metabolized by the mutant microorganism. A suitable media for growth of microorganisms under organosulfur conditions may suitably be a composition of mineral nutrients, such as 4 gms $K_2HPO_4$, 4 gms $Na_2HPO_4$, 2 gms $NH_4Cl$, 0.2 gm $MgCl_2.6H_2O$, 0.001 gm $CaCl_2.2H_2O$, and 0.001 gm $FeCl_3.6H_2O$ per liter of distilled, deionized water. Any assimilable carbon source devoid of sulfur may be used in amounts to support desired microbial growth. Suitable assimilable carbon sources include glucose, glycerol, sodium acetate, sodium benzoate, sodium succinate, and sucrose at concentrations of about 20 mM and benzene, ethanol, isobutanol, and toluene may be used as vapors in the head space of the bacterial growth bioreactors. Organosulfur compounds having organic C—S bonds are suitable, including benzothiophene, benzyldisulfide, dibenzothiophene, dibenzothiophene sulfone, phenyldisulfide, thianthrene, thioxanthene (Aldrich Chemical Company, Milwaukee, Wis.), dibenzothiophene sulfoxide (ICN Biomedicals, K&K Labs, Plainview, N.J.) and trithiane (Fairfield Chemical Company, P.O. Box 20, Clythewood, S.C.) may be used over concentration ranges which support microbial growth, in the order of about 20 mM and thiophene (Aldrich Chemical Company) may be used as a vapor. Nutrient broth (Difco Laboratories, Detroit, Mich.) or the above growth media solidified with about 15 g of agar (Difco) per liter may be employed for streaking or plating bacterial cultures. Bacterial growth may be monitored turbidimetrically using a Klett-Sommerson colorimeter or by enumerating colony forming units on appropriate agar.

Inoculum may be prepared by adding 5 gm samples of soil obtained from coal storage sites and from petroleum refinery sites to 10 ml of the above growth media, vortexed for 60 seconds, and allowed to settle for 30 minutes. The supernatants may be removed with a Pasteur pipette and used directly or diluted with an equal volume of nutrient broth and incubated at room temperature for about 24 to 48 hours before being used to inoculate the bioreactors.

Bioreactors/selectostats were of special design to provide continuous flow of liquid nutrients while retaining coal or organosulfur solids. The same batch of coal or organosulfur compound remains within the bioreactor for the duration of its operation whereas the aqueous phase media may be continuously supplied to the bioreactor. The retention of coal within the bioreactor for long periods of time may be accomplished by using relatively large particles of coal, typically $-9$ $+12$ mesh, and the use of an inclined, non-mixed sedimentation tube containing several weirs/baffles from which the bioreactor effluent may be withdrawn at relatively slow flow rates. The effluent withdrawal rates may be adjusted according to the ability of the microorganism to respond to the sulfur limitation challenge, typically, hydraulic retention times may be in the order of 72 hours.

The selectostats may be monitored frequently to determine suitable carbon source feed rate and to assay for presence of biologically available sulfur in the effluent. This may be achieved by centrifuging fresh bioreactor effluent to remove coal fines and particles of organosulfur substrate and bacteria followed by use of the supernatant in bacterial growth tests. Four cultures are prepared: the supernatant; the supernatant with 15 mM $SO_4$; a supernatant with 20 mM carbon source; and a supernatant with 15 mM $SO_4$ and 20 mM carbon source, each inoculated with a microbial culture at $10^5$ microorganism/ml and incubated for 2 to 5 days with shaking at growth temperatures for the microorganism being tested. Bacterial growth is monitored turbidimetrically or by determining colony-forming units. The carbon source sample serves to indicate the presence of biologically available sulfur in the effluent supernatant while the sample with added sulfate serves to indicate the presence of a carbon source in the effluent supernatant, and the sample containing both the carbon and added sulfate serves to indicate the presence of inhibitory substances in the effluent supernatant.

The ability of bacteria to utilize organic sulfur compounds for growth can be measured by the Sulfur Bioavailability Assay. This assay is based on the fact that all life requires some sulfur for growth and, therefore, a situation can be created whereby quantifying bacterial growth provides a measure of the utilization of any organic or inorganic compound as a source of sulfur. In practice, growth media containing a carbon source at 20 mM is used unamended, amended with 20 mM $Na_2SO_4$, and amended with 20 mM of an organosulfur compound or an inorganic sulfur compound. Each of the three conditions are then inoculated with a microbial culture at $10^5$ microorganisms/mL and incubated for 2 to 5 days with shaking at temperatures appropriate for the microorganism being tested. Bacterial growth is monitored turbidimetrically or by determining colony forming units. The unamended sample serves as a negative control while the sample amended with sulfate serves as a positive control, and both controls are used to assess whether bacterial growth occurred at the expense of sulfur obtained from the organosulfur test compound.

Development of the selective organic sulfur-specific culture may be accelerated by mutagenesis by exposure to 1-methyl-3-nitro-1-nitrosoguanidine (NTG) or to ultraviolet irradiation. Mutagenesis with NTG may be performed by spreading a solution of bacteria on an agar plate and placing a crystal of NTG in the center of the plate. During incubation, the NTG crystal dissolves in the agar forming a diffusional concentration gradient which results in no bacterial growth at the center and healthy growth at the outer perimeter of the plate. Between these extremes, a narrow zone of intermediate growth is readily observable and mutagenized bacteria are obtained from this zone. Bacteria for UV-mutagenesis may be pelleted from liquid culture by centrifugation, washed with the above growth media, and resuspended in a volume of the above growth media. Three milliliter portions may be placed in uncovered sterile petri dishes and exposed to doses of UV irradiation sufficient to cause 2 logs of killing, typically 10 $J/m^2$.

A mixed bacterial culture obtained from the selectostats after several months operation was shown to be capable of utilizing a range of organosulfur compounds as the sole source of sulfur as determined by the Sulfur Bioavailability Assay described above. Specific C—S bond cleavage in dibenzothiophene by this mixed culture was demonstrated by gas chromatographic/mass spectrometric analysis. Standard microbiological techniques were used to obtain pure cultures representative of each bacterial type present in the mixed culture. Each pure culture was individually tested for its ability to utilize organosulfur compounds as the sole source of sulfur by the Sulfur Bioavailability Assay. The only pure isolated culture which exhibited the ability to utilize organosulfur compounds as the sole source of sulfur was the mutant organic sulfur selective microorganism which has been identified as *Rhodococcus rhodochrous*. This *Rhodococcus rhodochrous* strain has been deposited with American Type Culture Collection and assigned number ATCC 53968. The strain is characterized by gram positive short rods of about $0.5\mu$ length, producing peach-colored colonies on nutrient agar and having high organic sulfur specificity by cleavage of C—S bonding.

To confirm the species identity, membrane lipids of the *Rhodococcus rhodochrous* ATCC 53968 were solvent extracted, derivated and analyzed by gas chromatography. The chromatogram was compared with lipid analyses of known Rhodococcus cultures recorded in a computer library supplied by Microcheck, Inc. (Northfield, Vt.). These tests identify ATCC 53968 as *Rhodococcus rhodochrous* as shown by Table 1 showing all fatty acids found in the extract compared with the library entry listed in elution order in the left column. An "x" is printed for each acid on the line opposite the fatty acid name indicating the amount of that acid and the library entry mean value for the acid identified with a "+". In cases where the library mean percentage and the actual percentage in the extract are the same an "*" is printed. A dashed line gives a +2 or −2 standard deviation window around the mean value for the library entry. Examination of Table 1 shows high certainty in the identification of the *Rhodococcus rhodochrous*.

TABLE 1

Membrane Lipid Analysis of *Rhodococcus rhodochrous* ATCC No. 53968

| Lipid Type | 0 | 5 | 10 | 15 | 20 | 25 | 30 | 35 | 40 | 45 | 50 |
|---|---|---|---|---|---|---|---|---|---|---|---|
| 14:0 | — — + x — — | | | | | | | | | | |
| 15:0 | — — * — — — — | | | | | | | | | | |
| 16:1 B | * — — | | | | | | | | | | |
| 16:1 CIS 9 | — — x + — — — — | | | | | | | | | | |
| 16:0 | | | | | | | — — — — — + — — x — — | | | | |
| 17:1 ISO6 | * — — | | | | | | | | | | |
| 17:1 B | — — — + x — — | | | | | | | | | | |
| unknown 16.918 | * — — | | | | | | | | | | |
| 17:0 | — — * — — | | | | | | | | | | |

TABLE 1-continued

Membrane Lipid Analysis of
Rhodococcus rhodochrous ATCC No. 53968
Percentage

```
Lipid Type        0    5    10   15   20   25   30   35   40   45   50
18:1 ISO F       —*——
18:1 CIS 9                            ————x————+—————————
18:0             ——x+——
10 Me 18:0                        ————————*————————
19:0 +—— x
20:0             —+x——
SUMMED FEATURE 4     ——x————+—————————
SUMMED FEATURE 8  —*————
```

Rhodococcus ATCC 53968 was compared with other Rhodococcus species obtained from American Type Culture Collection with respect to carbon sources which would support the growth of these cultures. The cultures were streaked onto the specified agar plates containing the indicated carbon sources and/or inoculated into liquid medium and evaluated after incubating the cultures for 96 hours at 30° C. The results of carbon source utilization studies using a variety of Rhodococcus strains are shown in Table 2. It appears entirely consistent from carbon sources which support the growth of the microorganism that Rhodococcus rhodochrous ATCC 53968 is in fact Rhodococcus rhodochrous.

Each of the Rhodococcus species listed in Table 2 were evaluated using the above described sulfur bioavailability assay to determine their ability to utilize organically bound sulfur in DBT. Most strains were tested several times using a variety of substrates. The ATCC 53968 strain was the only Rhodococcus species tested having the C—S bond cleavage property. Additional tests with Rhodococcus rhodochrous ATCC 53968 have shown that trithiane, thianthrene, dibenzothiophene sulfoxide and dibenzothiophene-sulfone and other organosulfur compounds may also be used as sulfur sources for Rhodococcus rhodochrous ATCC 53968.

The Rhodococcus rhodochrous ATCC 53968 strain has shown a doubling time in the presence of both dibenzothiophene and inorganic sulfate to be about 12 hours. The growth rate of Rhodococcus rhodochrous ATCC 53968 is much faster on rich medium (Luria Broth), however, other microorganisms exhibit even faster growth rates on the rich medium.

The stability of the desulfurization trait of Rhodococcus rhodochrous ATCC 53968 has been evaluated by growing the culture under non-selective conditions for multiple generations and more than 200 single colonies were obtained and tested by the above described sulfur bioavailability assay, all cultures proving to be competent for desulfurization by C—S bond cleavage. It appears that under the above culture conditions, the C—S bond cleavage ability possessed by the Rhodococcus rhodochrous ATCC 53968 is a stable trait. The desulfurization trait of Rhodococcus rhodochrous ATCC 53968 is maintained through heat shocking. Growth of Rhodococcus rhodochrous ATCC 53968 is severely retarded or absent at 37° and 42° C. when incubated at those temperatures for 48 hours. Seventy-two single colonies of desulfurization competent Rhodococcus rhodochrous ATCC 53968 have been streaked onto nutrient agar, incubated at 37° C. or 42° C. for 48 hours followed by incubation at 30° C. for 72 hours and tested by the above described sulfur bioavailability assay, with all colonies exhibiting stable maintenance of the desulfurization trait.

The mutant culture Rhodococcus rhodochrous ATCC 53968 was inoculated into a mineral salts glucose bacterial growth medium containing dibenzothiophene as the sole sulfur source. After growth at 30° C. for 72 hours, the cultures were centrifuged, the supernatants processed by solid-phase extraction using C-18 silica compounds, eluted with dichloromethane, and analyzed using gas chromatography/mass spectrometry to identify and quantify the metabolites of dibenzothiophene. The results are shown in Table 3, quantitation of the metabolites being accomplished by spiking the dichloromethane eluates with a known concentration of ethyl-napthalene and comparing metabolite peaks with retention times and concentration curves prepared with pure chemical compounds. Compounds that were specifically looked for are listed in Table 3. The face that only 2-hydroxybiphenyl was found and that 3-hydroxy-2-formyl-benzothiophene and any other compounds known to be formed in the carbon destructive pathway of DBT degradation were not found demonstrates that the Rhodococcus rhodochrous ATCC 53968 metabolizes dibenzothiophene via C—S bond cleavage route and not by a C—C bond cleavage route as do many of the microorganisms of the prior art.

TABLE 2

| Rhodococcus strains | ATCC # | Glycerol | Sucrose | Citrate | Benzoate | Acetate | Glucose | Ethanol | Succinate | Isobutanol |
|---|---|---|---|---|---|---|---|---|---|---|
| R. rhodochrous | 53968 | ++ | +/− | − | ++ | + | + | + | − | + |
| R. rhodochrous | 13808 | +/− | +/− | − | ++ | + | + | + | + | +++ |
| R. rhodochrous | 19149 | − | + | + | ++ | + | +++ | +++ | + | +++ |
| R. rhodochrous | 19067 | − | + | − | ++ | + | + | +++ | + | +++ |
| R. erythropolis | 19369 | +/− | − | +/− | − | + | ++ | +++ | + | +++ |
| R. erythropolis | 4277 | − | − | − | +/− | + | + | ++ | + | ++ |
| R. globerulus | 19370 | + | + | +/− | ++ | + | + | ++ | + | ++ |
| R. globerulus | 15903 | +++ | + | − | ++ | + | ++ | +++ | + | +++ |
| R. equi | 14887 | − | +/− | − | +/− | − | + | − | − | − |

TABLE 3

METABOLITES OF RHODOCOCCUS RHODOCHROUS

| Compound | ATCC 53968 Mol. Wt. | ppm |
|---|---|---|
| * Dibenzothiophene-5-oxide | 200 | BDL |
| plus Phenoxathiin | 200 | |

TABLE 3-continued

METABOLITES OF *RHODOCOCCUS RHODOCHROUS*

| Compound | ATCC 53968 Mol. Wt. | ppm |
|---|---|---|
| ** Dihydroxybiphenyl | 186 | BDL |
| ** 2-hydroxybiphenyl | 170 | 35.27 |
| + 3-hydroxy-2-formyl-benzothiophene | 178 | BDL |
| ** Biphenyl | 154 | BDL |
| + Benzothiophene | 134 | BDL |
| + Three isomers of $C_8H_6OS$: (hydroxybenzothiophene) | | |
| No. 1 | 150 | BDL |
| No. 2 | 150 | BDL |
| No. 3 | 150 | BDL |
| + $C_9H_8OS$ | 164 | BDL |
| + $C_9H_8O_2S$ | 180 | BDL |
| + $C_9H_6OS$ | 162 | BDL |
| + $C_{10}H_{10}OS$ or $C_9H_6O_2S$ | 178 | BDL |
| + $C_8H_8O_2S$ isomers a) | 168 | BDL |
| b) | 168 | BDL |
| + Formula (?) | 220 | BDL |

\* C-S cleavage intermediate
\*\* C-S cleavage product
+ C-C cleavage product
BDL means below detection level of ~0.001

The presence of high concentrations of sulfate, more than 20 mM, inhibits desulfurization of DBT and desulfurization does not take place in rich bacterial growth medium by *Rhodococcus rhodochrous* ATCC 53968. The minimum sulfate requirement for bacterial growth in a test tube/shake flask is about 0.25 to 1.0 mM and the presence of that amount of available sulfur does not inhibit organic desulfurization and may stimulate organic desulfurization by allowing more vigorous growth, however, high levels of sulfate inhibit or repress the desulfurization of DBT by *Rhodococcus rhodochrous* ATCC 53968, even though excellent growth occurs. The complete lack of DBT's desulfurization when *Rhodococcus rhodochrous* ATCC 53968 is grown in a rich bacterial medium suggests that some amount of starvation/stress is required to obtain an expression of the desulfurization trait and that DBT is not capable of inducing the desulfurization trait of that microorganism. *Rhodococcus rhodochrous* ATCC 53968 was inoculated into a mineral salts bacterial growth medium or a rich medium as indicated in Table 4 and after growth at 30° C. for 72 hours, the samples were analyzed by gas chromatography/mass spectrometry to identify and quantify metabolites of DBT. The results are shown in Tab 4.

TABLE 4

| Sample | Defined Medium | Rich Medium | Inoculum | DBT | Sulfate | 2-hydroxybiphenyl micrograms/mL |
|---|---|---|---|---|---|---|
| 1 | + | | ATCC 53968 | + | 0 | 29.6 |
| 2 | + | | ATCC 53968 | − | 0 | BDL* |
| 3 | + | | ATCC 53968 | + | 20 mM | 4.8 |
| 4 | | + | ATCC 53968 | + | ≧20 mM | BDL* |
| 5 | | + | ATCC 53968 | + | ≧20 mM | BDL* |
| 6 | | + | None | − | ≧20 mM | BDL* |

*Below Detectable Level

Microorganisms which have the ability of selective cleavage of organic C—S bonds when grown in a growth medium comprising mineral nutrients and an assimilable source of carbon in the presence of oxygen and the substantial absence of sulfur-containing compounds except the sulfur-containing organic carbonaceous material are suitable for selective cleavage of organic C—S bonds and selectively reducing the sulfur content of sulfur-containing carbonaceous material according to the process of this invention. *Rhodococcus rhodochrous* ATCC No. 53968 and its derivatives as described above and *Bacillus sphaericus* ATCC No. 53969 and its derivatives as more fully described in copending, commonly owned application Ser. No. 07/640,931 now U.S. Pat. No. 5,198,341, incorporated herein by reference, have been found to be preferred microorganisms for the process of this invention.

*Rhodococcus rhodochrous* ATCC 53968 derivatives have been shown to retain the same or better selective desulfurization trait of the ATCC 53968 strain. Derivative microorganisms of *Rhodococcus rhodochrous* ATCC 53968 have been obtained which have additionally exhibited resistance to the antibiotics ampicillin, cephalordine, naladixic acid, spectinomycin, streptomycin, rifampicin, and combinations of two or three of these resistance traits. These antibiotic resistant derivatives are the result of genetic mutations, although not the product of recombinant DNA techniques. Other derivative microorganisms of *Rhodococcus rhodochrous* ATCC 53968 have been demonstrated to be auxotrophic mutants/derivatives defective in the ability to synthesize one or more essential amino acid or vitamin. Some of the auxotrophic mutant derivatives have been exhibited to be defective in their ability to synthesize sulfur-containing amino acids cysteine and methionine. All of the *Rhodococcus rhodochrous* ATCC 53968 derivative microorganisms exhibiting antibiotic resistance and auxotrophic properties have retained their ability to cleave organic C—S bonds.

I have found tolyldisulfide to specifically inhibit the organic C—S bond cleavage trait of *Rhodococcus rhodochrous* ATCC 53968 when present with another organic sulfur-containing compound, such as dibenzothiophene. However, tolyldisulfide is not generally inhibitory to *Rhodococcus rhodochrous* ATCC 53968 since it does not inhibit utilization of inorganic sulfate for growth. Mutants/derivatives of *Rhodococcus rhodochrous* ATCC 53968 have been selected which overcome such inhibition of the organic C—S bond cleavage trait and were able to grow with tolyldisulfide as their sole source of sulfur. Such derivatives have exhibited about a 25 percent enhancement in their ability to metabolize dibenzothiophene by organic C—S bond cleavage.

Another derivative culture of *Rhodococcus rhodochrous* ATCC 53968 has been isolated which exhibits the organic C—S bond cleavage trait in the presence of high levels, in the order of about 20 mM, of inorganic sulfate. The microorganism *Rhodococcus rhodochrous* ATCC 53968 itself exhibits reduction in the organic C—S bond cleavage trait in such concentrations of inorganic sulfate.

An antibiotic resistant derivative of ATCC 53968 was used in mixed culture with *Enterobacter aerogenes*. The mixed inoculum contained a tenfold excess of ATCC 53968 relative to *E. aerogenes* and growth was monitored in the above defined growth medium, glycerol, and DBT as the sole source of sulfur. At 50, 70, 140 and 240 hours samples of the culture were used to prepare dilution series which were plated onto nutrient agar and nutrient agar containing 250 micrograms/mL streptomycin. *E. aerogenes* grew faster than the ATCC 53968 derivative on the nutrient agar while only the ATCC 53968 derivative grew on nutrient agar containing antibiotic. ATCC 53968 derivative grew rapidly during the first 70–80 hours since it is the only organism capable of metabolizing sulfur from DBT. However, after about 50–60 hours, even though *E. aerogenes* cannot metabolize DBT, it begins rapid growth and at 240 hours is present in nearly three orders of magnitude greater abundance than the ATCC 53968 derivative. This suggests that DBT is metabolized in association with the outer surface of the ATCC 53968 bacteria in a manner such that sulfur liberated from DBT by ATCC 53968 is available for metabolism by other bacteria.

*Rhodococcus rhodochrous* ATCC 53968 and its derivatives and *Bacillus sphaericus* ATCC 53969 and its derivatives may be used for the highly efficient removal of organic sulfur from organic sulfur-containing carbonaceous materials, particularly naturally occurring fossil fuels such as coal, petroleum, shale, oil, lignite, and synthetic fuels derived therefrom. The organic sulfur may be selectively removed from such materials by contacting with *Rhodococcus rhodochrous* ATCC 53968 and/or its derivatives in an aqueous media at temperatures up to about 42° C. The organic sulfur removal from such materials may be obtained by selective metabolism of the organic sulfur from the solid organic sulfur-containing compounds with the *Rhodococcus rhodochrous* ATCC 53968 and/or its derivatives in an aqueous growth medium comprising suitable mineral nutrients and an assimilable source of carbon. The metabolism is under aerobic conditions requiring oxygen with the pH of the aqueous growth media maintained at about a pH of 5 to 8 and preferably about 6 to 7, and a temperature of about 15° to 34° C., preferably about 28° to 32° C. The higher temperature ranges result in faster metabolism, however, the microorganisms are known to not tolerate temperatures in the order of 37° C. The aqueous media should contain a suitable concentration of microorganisms to achieve the desired selective sulfur removal within the desired time interval.

I have found that *Rhodococcus rhodochrous* ATCC 53968 and its derivatives and Bacillus sphaericus ATCC 53969 and its derivatives uniquely metabolize sulfur by cleavage of the C—S bonding in organic carbonaceous materials; for example, in the metabolism of dibenzothiophene, the organic end product is 2-hydroxybiphenyl. These properties of the microorganism metabolism render these microorganisms and their derivatives specific agents for use in organic chemical synthesis for cleavage of organic C—S bonding which may be used in various organic process synthesis systems. Likewise, the unique properties of these microorganisms and their derivatives may be utilized in desulfurizing degradation of a wide variety of organic materials by cleavage of organic C—S bonding in recycling operations, such as in breakdown of sulfur containing organic molecules such as in rubber products.

The microbiological process of this invention results in the conversion of organic sulfur to inorganic sulfate. Sulfur in the form of organically bound sulfur presents very difficult separation, while the inorganic sulfate produced by this process may be easily removed by a wide variety of methods readily apparent to one of ordinary skill in the art.

While in the foregoing specification this invention has been described in relation to certain preferred embodiments thereof, and many details have been set forth for purpose of illustration it will be apparent to those skilled in the art that the invention is susceptible to additional embodiments and that certain of the details described herein can be varied considerably without departing from the basic principles of the invention.

I claim:

1. A process for cleavage of organic C—S bonds comprising:
    contacting an organic carbonaceous material selected from the group consisting of oil and coal having C—S bonds with microorganisms selected from the group consisting of *Rhodococcus rhodochrous* strain ATCC No. 53968 having a capability for selective cleavage of organic C—S bonds while leaving C—C bonds intact, a mutant microorganism of *Rhodococcus rhodochrous* strain ATCC No. 53968 having the capability of the parent microorganism for selective cleavage of organic C—S bonds while leaving C—C bonds intact, and mixtures thereof under metabolic conditions for said *Rhodococcus rhodochrous* suitable for cleaving said organic C—S bonds in a growth medium comprising mineral nutrients and an assimilable source of carbon in substantial absence of a sulfur-containing compound except said organic carbonaceous material and in the presence of oxygen wherein said microorganism cleaves said C—S bonds.

2. A process for cleavage of organic C—S bonds comprising:
    contacting an organic carbonaceous material selected from the group consisting of oil and coal having C—S bonds with microorganisms selected from the group consisting of *Rhodococcus rhodochrous* strain ATCC No. 53968 having a capability for selective cleavage of organic C—S bonds while leaving C—C bonds intact, a mutant microorganism of *Rhodococcus rhodochrous* strain ATCC No. 53968 having the capability of the parent microorganism for selective cleavage of organic C—S bonds while leaving C—C bonds intact, and mixtures thereof under metabolic conditions for said *Rhodococcus rhodochrous* suitable for cleaving said organic C—S bonds at a temperature from about 20° to about 34° C. in a growth medium comprising mineral nutrients and an assimilable source of carbon in substantial absence of a sulfur-containing compound except said organic carbonaceous material and in the presence of oxygen wherein said microorganism cleaves said C—S bonds.

3. A process according to claim 2 wherein said metabolic conditions include the pH being maintained at about 6 to about 7.

4. A process according to claim 3 wherein the temperature is maintained at about 30° to about 32° C.

5. A process according to claim 2 wherein the temperature is maintained at about 30° to about 32° C.

6. A process for cleavage of organic C—S bonds comprising:
    contacting an organic compound selected from the group consisting of aromatic and cyclic aliphatic carbonaceous material having C—S bonds selected from the group consisting of dibenzothiophene, dibenzothiophene sulfone, thianthrene, dibenzothiophene sulfoxide, trithiane, and mixtures thereof with microorganisms selected from the group consisting of *Rhodococcus rhodochrous* strain ATCC No. 53968 having a capability for selective cleavage of organic C—S bonds while leaving C—C bonds intact, a mutant microorganism of *Rhodococcus rhodochrous* strain ATCC No. 53968 having the capability of the parent microorganism for selective cleavage of organic C—S bond while leaving C—C bonds intact, and mixtures thereof, said contacting being performed under metabolic conditions for said microorganism suitable for cleaving said organic C—S bonds in a growth medium comprising mineral nutrients and an assimilable source of carbon in substantial absence of a sulfur-containing compound except said organic carbonaceous material and in the presence of oxygen wherein said microorganism cleaves said C—S bonds.

7. A process according to claim 6 wherein said metabolic conditions include the temperature being maintained at about 20° to about 34° C.

8. A process according to claim 6 wherein said metabolic conditions include the temperatures being maintained at about 30° to about 32° C.

9. A process according to claim 6 wherein said metabolic conditions include the pH being maintained at about 6 to about 7.

* * * * *